United States Patent [19]
Wikeley

[11] Patent Number: 6,107,249
[45] Date of Patent: Aug. 22, 2000

[54] GLYPHOSATE FORMULATIONS

[75] Inventor: Philip Simon Wikeley, Loughborough, United Kingdom

[73] Assignee: ZENECA Limited, United Kingdom

[21] Appl. No.: 09/284,106

[22] PCT Filed: Oct. 3, 1997

[86] PCT No.: PCT/GB97/02720

§ 371 Date: Apr. 7, 1999

§ 102(e) Date: Apr. 7, 1999

[87] PCT Pub. No.: WO98/15181

PCT Pub. Date: Apr. 16, 1998

[30] Foreign Application Priority Data

Oct. 7, 1996 [GB] United Kingdom ............... 9620849
Mar. 7, 1997 [GB] United Kingdom ............... 9704753

[51] Int. Cl.$^7$ .................. A01N 25/30; A01N 57/02
[52] U.S. Cl. ............................ 504/206; 504/362
[58] Field of Search .............................. 504/206

[56] References Cited

U.S. PATENT DOCUMENTS 5,612,285  3/1997  Arnold ........................... 504/206
5,888,934  3/1999  Townson et al. ............... 504/206

FOREIGN PATENT DOCUMENTS 2 119 518   9/1994   Canada .
96/34078   10/1996   WIPO .

*Primary Examiner*—S. Mark Clardy
*Attorney, Agent, or Firm*—David P. LeCroy

[57] ABSTRACT

A low-foam, physically stable composition comprises (i) N-phosphonomethylglycine acid or a water-soluble salt thereof (ii) an alkylglycoside surfactant which is preferably 2-ethyl-1-hexyl glycoside having a degree of polymerization of from 1 to 2 and (iii) a quaternary ammonium salt surfactant such as a dialkyldimethylammonium salt wherein the sum of the carbon atoms in the dialkyl groups is from 12 to 20 or an alkyltrimethylammonium salt wherein the alkyl group contains from 4 to 12 carbon atoms.

11 Claims, No Drawings

GLYPHOSATE FORMULATIONS

This application has been filed under 35 U.S.C. §317 as a national stage application of international application PCT/GB97/02720, filed Oct. 3, 1997.

This invention relates to glyphosate formulations and in particular to low-foam glyphosate formulations. Glyphosate (N-phosphonomethylglycine) in the form of the acid or its water-soluble salts is a widely used herbicide which is commercially available in a variety of formulations. Many more formulations have been proposed in the patent or academic literature. Except in a few limited markets for which the herbicide is sold diluted and ready to use, glyphosate formulations are generally concentrated and designed to be diluted prior to use. The concentrated formulation will normally contain one or more surfactants which are designed not only to improve biological activity but also a whole range of physical parameters such as stability, sprayability, wettability of the plants, rainfastness and many other factors. Modern formulations are therefore complex and may contain a number of different surfactants and adjuvants. Ideally, all components are built in to the concentrate which is then simply diluted ready for use. However, in commercial practice the concentrate must be able to withstand storage for prolonged periods and at extremes of temperature without adverse effect such as the separation of the components. It may not therefore be possible to include all desired components within the commercial concentrate and it is often the case that the concentrate will contain one or more of the principal surfactants or adjuvants and that others will be added during the tank mix when the concentrate is diluted prior to use.

Surfactants and adjuvants are designed to improve biological and other factors by altering the interfacial properties of the composition and a problem frequently encountered with agrochemical formulations is that of foaming of the concentrate or, more commonly, foaming in the spray tank when the composition is diluted. Foaming may be exacerbated when the dilution of the composition is accompanied by agitation to ensure efficient mixing of the concentrate in the water. Foaming is not generally an insurmountable problem and may be controlled by efficient spray tank design and appropriate dilution and mixing methods. Anti-foam additives may also be used but such anti-foams are expensive and may themselves be incompatible with the composition. Furthermore once foam starts to be produced, high levels of anti-foam may be required to control it. Excessive foaming can be very annoying for the user and may result in the loss of active ingredient or of surfactant which may concentrate in the foam, thereby reducing bio-activity. Foaming may also introduce undesirable delay before the spray solution is ready for use since the farmer must wait for the foam to subside before continuing to fill the spray tank There is a need therefore for a glyphosate concentrated formulation which combines high biological activity and other desirable features with low-foaming properties in the concentrate and on dilution of the concentrate with water. A low-foam composition which is storage stable and which contains all desired adjuvants and surfactants, requiring the addition of no extra components in the tank mix, presents a particular challenge. The difficulty of obtaining a such a composition increases still further as the concentration of the composition is increased to meet the market need for high strength formulations.

According to the present invention there is provided a low-foam composition comprising (i) N-phosphonomethylglycine acid or a water-soluble salt thereof (ii) an alkylglycoside surfactant and (iii) a quaternary ammonium salt surfactant.

The low-foam composition is preferably a physically stable concentrate suitable for dilution and application as an agricultural spray.

The quaternary ammonium salt surfactant is suitably a compound of formula $R^1R^2R^3R^4N^+X^-$ wherein $X^-$ is an agrochemically acceptable anion, for example a halide anion such as chloride or bromide and either (i) $R^1$ and $R^2$ which may be the same or different are lower alkyl groups such as methyl or ethyl, $R^3$ and $R^4$, which may be same or different, are branched or linear alkyl groups each containing from 6 to 18 carbon atoms, or (ii) $R^1$ and $R^2$ and $R^3$ which may be the same or different are lower alkyl groups such as methyl or ethyl and $R^4$ is a branched or linear alkyl group containing 4 to 12 atoms and more preferably 6 to 12 carbon atoms. The term "lower alkyl group" indicates an alkyl group containing from 1 to 4 carbon atoms.

The term "alkylglycoside" as used herein includes alkyl polyglycoside surfactants and alkylmonoglycoside surfactants. Alkylglycosides have the general formula (I)

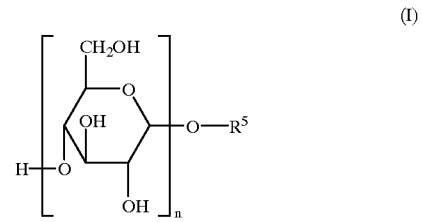

wherein n is the degree of polymerisation and is typically within the range from 1 to 3, for example from 1 to 2, and $R^5$ is a branched or straight chain alkyl group having from 4 to 18 carbon atoms or a mixture of alkyl groups having an average value within the given range. Typical of alkylpolyglycosides is the product commercially available under the trade names AL2042 (Imperial Chemical Industries PLC) and AGRIMUL PG2067 (Henkel Corp) wherein n is an average of 1.7 and $R^5$ is a mixture of octyl (45%) and decyl (55%).

Preferably $R^5$ in formula (I) above is a branched chain alkyl group containing from 4 to 18 carbon atoms or a mixture of alkyl groups having an average value within the given range. A preferred form of branching involves one straight chain branch in the 2- position. An especially preferred group $R^5$ is 2-ethyl-1-hexyl. Such alkylglycosides wherein $R^5$ is 2-ethyl-1-hexyl and the degree of polymerisation is from 1 to 2, for example about 1.6 (referred to herein as 2-ethyl-1-hexyl glycoside), have inherently low-foaming properties as compared with more conventional alkylglycoside surfactants such as those mentioned above. We have found however that this potential advantage is offset by a number of important disadvantages. In particular low-foaming alkylglycosides such as 2-ethyl-1-hexyl glycoside have been found to suffer from the following disadvantages when used as the sole surfactant in combination with typical glyphosate salts:

1. The composition has a noticeably lower herbicidal activity as compared with a corresponding composition containing more conventional alkylglycosides. Typically the herbicidal activity may be reduced by up to 20% depending on the species treated.
2. 2-Ethyl-1-hexylglycoside is not an homogeneous product (it is a mixture of diastereoisomers) and it has to be warmed to about 30° C. prior to incorporation in the composition.

3. The surfactant is incompatible with typical glyphosate salts below about 10° C. In commercial practice it is desirable to maintain physical stability of the concentrated formulation to a temperature of about −10° C.

4. Despite the inherent low-foaming properties of the 2-Ethyl-1-hexylglycoside, undesirable foaming can still be observed in the concentrated formulation itself.

A wide range of possible co-surfactants were evaluated in an attempt to alleviate some or all of these problems but it was found that most surfactants tended if anything to increase the foaming and did not improve the physical stability of the concentrated formulation. Surprisingly, the quaternary ammonium salt surfactants of the present invention were found to provide a physically stable and low-foaming composition in which at least some of the above problems were alleviated and in which the foaming of the composition may even be reduced still further.

Thus according to a further aspect of the present invention there is provided a low-foam, physically stable concentrated composition comprising (i) N-phosphonomethylglycine acid or a water-soluble salt thereof (ii) an alkylglycoside surfactant and (iii) a quaternary ammonium salt surfactant of formula $R^1R^2R^3R^4N^+ X^{31}$ wherein X is an agrochemically acceptable anion, for example a halide anion such as chloride or bromide and either (i) $R^1$ and $R^2$ which may be the same or different are lower alkyl groups such as methyl or ethyl, $R^3$ and $R^4$, which may be same or different, are branched or linear alkyl groups each containing from 6 to 18 carbon atoms, or (ii) $R^1$ and $R^2$ and $R^3$ which may be the same or different are lower alkyl groups such as methyl or ethyl and $R^4$ is a branched or linear alkyl group containing 4 to 12 atoms and more preferably 6 to 12 carbon atoms.

Branched chain alkyl groups and indicated herein by the appropriate designation, such as "isoalkyl", and where no designation is indicated, the alkyl group may be taken to be linear.

Preferred quaternary ammonium salt surfactants are dialkyldimethylammonium salts wherein $R^1$ and $R^2$ are methyl and $R^3$ and $R^4$ are as defined or alkyltrimethylammonium salts wherein $R^1$ and $R^2$ and $R^3$ are methyl and $R^4$ is as defined and is preferably a linear alkyl group.

As noted above, a preferred alkylglycoside surfactant is 2-ethyl-1-hexylglycoside.

When used with 2-ethyl-1-hexyl-glycoside, didecyldimethylammonium salts are readily built in to the concentrated formulation and assist in reducing foaming in the concentrate itself, although foaming on dilution may still be experienced. Similarly, di(coco)dimethylammonium salts (wherein $R^3$ and $R^4$ are derived from cocoamine and contain typically 58% C12, 22% C14 with minor proportions of C10, C16 and C18) assist in reducing foaming in the concentrate itself but are less readily built into the concentrate composition than are lower dialkyl chain quaternary ammonium salts. Thus it is preferred that when the quaternary ammonium salt surfactant is a dialkyldimethylammonium salt, $R^3$ and $R^4$ are alkyl groups wherein the sum of the carbon atoms in $R^3$ and $R^4$ is from 12 to 20, for example from 16 to 19. In general the sum of $R^3$ and $R^4$ may be greater if the alkyl groups are branched than if they are linear. Especially preferred dialkyldimethylammonium salts are dioctyldimethylammonium salts, N-decyl,N-isononyldimethylammonium salts and di-isononyldimethylammonium salts. Salts are generally commercially available as the chloride.

When the quaternary ammonium salt is an alkyltrimethylammonium salts $R^4$ is an alkyl group containing from 4 to 12 carbon atoms. Thus when used with 2-ethyl-1-hexylglycoside for example, we have found if $R^4$ is an alkyl group containing 14 or more carbon atoms the quaternary ammonium salt may assist in building the glyphosate salt into a concentrated composition but does not assist in reducing foaming on dilution. The same has been observed when $R^4$ is an alkyl group derived from cocoamine which, as noted above, contains a majority (58%) of C12 but a significant proportion (22%) of C14 alkyl groups.

Especially preferred alkyltrimethylammonium salts are n-octyltrimethylammonium salts, n-decyltrimethylammonium salts and n-dodecyltrimethylammonium salts.

In particular it is a formidable problem to provide a composition which retains low-foam properties both in the concentrate and on dilution, which is physically stable within the temperature range encountered in commercial practice and which synergystically enhances the activity of the formulation as compared with the use of the alkylglycoside on its own. Surprisingly, preferred dialkyldimethylammonium salts and alkyltrimethylammonium salts according to the invention in combination with 2-ethyl-1-hexyl glycoside have been found to be essentially unique in meeting all these requirements.

It is especially preferred that the alkyl glycoside is 2-ethyl-1-hexylglycoside and is used in combination with dioctyldimethylammonium chloride.

We have found that a glyphosate composition of the present invention containing the combination of 2-ethyl-1-hexyl glycoside and a preferred dialkyldimethylammonium salt or alkyltrimethylammonium salt provides a concentrated composition which does not itself foam and is exceptionally low-foaming on dilution. Preferred compositions of the invention are even less foaming than is a corresponding formulation containing only the 2-ethyl-1-hexyl glycoside. Moreover, the concentrated formulation is storage stable over the range of temperatures likely to be encountered in commercial practice and remains storage stable even when containing relatively high concentrations of the N-phosphonomethylglycine component. Furthermore, whereas a composition containing only the N-phosphonomethylglycine and 2-ethyl-1-hexylglycoside has a reduced overall herbicidal activity as compared with conventional compositions containing N-phosphonomethylglycine and an alkylpolyglycoside such as AL2042, we have found that compositions of the present invention containing the combination of 2-ethyl-1-hexylglycoside and a preferred quaternary ammonium salt such as dioctyldimethylammonium chloride shows overall herbicidal activity which is greater than that of the corresponding composition in which the dioctyldimethylammonium salt is omitted and which is comparable to that of commercially available compositions which either exhibit relatively high foaming characteristics or require the incorporation of an expensive anti-foam.

It is a still further advantage of such a combination that mixtures of 2-ethyl-1-hexylglycoside and preferred quaternary ammonium salts are homogeneous and storage-stable and may readily be incorporated into the composition, thereby providing a significant manufacturing advantage as compared with the 2-ethyl-1-hexylglycoside used on its own.

It is to be understood that alkyl groups $R^3$ and $R^4$, for example octyl groups $R^3$ and $R^4$, may be a mixture of isomers and indeed may be a mixture of alkyl groups of different chain lengths having an average value of 8. Thus there may be slight differences in composition and performance of dialkyldimethylarnmonium chloride obtained from different sources.

Preferably there is used a water-soluble salt of glyphosate. Any of the commonly available salts of glyphosate may be used in the composition of the present invention, including for example the trimethylsulphonium salt, the isopropylamine salt, ammonium salt and alkali metal salts. The content of the water-soluble salt of glyphosate in the composition is expressed herein in terms of the glyphosate acid equivalent, which is the weight of glyphosate acid contained within the given water-soluble salt.

The composition of the present invention is suitably a liquid concentrate which is diluted in water prior to use. Typical concentrations of glyphosate in the concentrate (expressed in g/l glyphosate acid equivalent) are from 50 to 500. Compatibility problems clearly tend to increase as the concentration of the glyphosate increases and it is an advantage of the present invention that storage-stable compositions may be obtained having a glyphosate content in the upper part of this range.

Preferably the composition of the present invention contains from 20 parts by weight of alkylglycoside per 100 parts by weight of glyphosate acid equivalent to 100 parts by weight of alkylglycoside per 100 parts by weight of glyphosate acid equivalent, although it will be appreciated that the use of high concentrations of glyphosate may limit the quantity of alkylglycoside which can be built into the formulation. It is especially preferred that the composition of the present invention contains from 50 parts by weight of alkylglycoside per 100 parts by weight of glyphosate acid equivalent to 70 parts by weight of alkylglycoside per 100 parts by weight of glyphosate acid equivalent The upper limit of the content of quaternary ammonium salt in the concentrated composition is that at which it is no longer compatible with the formulation and separates out. In general we have found that a higher proportion of alkyltrimethylammonium salt may be used in the composition than of dialkyldimethylarnmonium salts. Typically the composition of the present invention contains from about 1 part by weight of quaternary ammonium salt per 100 parts by weight of alkylglycoside to about 100 parts by weight of quaternary ammonium salt per 100 parts by weight of alkylglycoside and especially from 10 parts by weight of quaternary ammonium salt per 100 parts by weight of alkylglycoside to 60 parts by weight of quaternary ammonium salt per 100 parts by weight of alkylglycoside.

Compositions of the present invention are active against a broad range of weed species including monocotyledonous and dicotyledonous species. The compositions of the present invention are suitably applied directly to unwanted plants (post-emergence application).

Thus according to a further aspect of the present invention there is provided a process of severely damaging or killing unwanted plants which comprises applying to the plants a herbicidally effective amount of a composition of the present invention.

EXAMPLE 1

The relative foaming of glyphosate concentrated compositions on dilution to the indicated level (w/w based on total product) was determined by the standard laboratory method as set out in CIPAC MT 47.2 (Collaborative International Pesticides Analytical Council Limited, Handbook page 2249. CIPAC method 1982, prepared by the Suspension Concentrates Panel of PAC-GB, Chairman E J Skerrett Long Ashton Research Station ). The results are presented in Table 1 and are given in terms of the volume of foam generated and remaining after 10 seconds and one minute respectively. A foam volume of 0 indicates that at least 40–50% of the surface was foam-free. If the foam was collapsing too rapidly to measure after 10 seconds, the time taken to obtain a clear surface is quoted (for example as "Clear 16 sec") in place of the Foam Volume. Since the foaming may be dependent on water hardness, experiments used either "CIPAC Standard Hard Water C" (shown as "SHW C" in the table) or deionised water.

| Composition* | Water type | Dilution (% w/w) | Foam Volume (/ml) after 10 seconds | Foam Volume (/ml) after 1 minute |
|---|---|---|---|---|
| 1.1 | SHW C | 1 | Clear 16 sec | 0 |
| 1.2 | SHW C | 1 | Clear 11 sec | 0 |
| 1.3 | SHW C | 1 | Clear 10 sec | 0 |
| 1.1 | SHW C | 5 | 14 | 6 |
| 1.1 | Deionised | 1 | Clear 12 sec | 0 |
| 1.1 | Deionised | 5 | 12 | 10 |
| 1.4* | SHW C | 1 | 8 | 6 |
| 1.4* | SHW C | 5 | 50 | 48 |
| 1.5 | SHW C | 1 | 70 | 0 |
| 1.6 | SHW C | 1 | 0 | 0 |
| 1.7 | SHW C | 1 | >100 | >100 |
| 1.8* | SHW C | 1 | 50 | 18 |
| 1.9 | SHW C | 1 | 70 | 70 |
| 1.10 | SHW C | 1 | 66 | 66 |
| 1.11 | SHW C | 1 | 0 | 0 |
| 1.12 | SHW C | 1 | Clear 14 sec | 0 |
| 1.13 | SHW C | 1 | 14 | 4 |
| 1.14 | SHW C | 1 | 10 | 8 |
| 1.15 | SHW C | 1 | 4 | 2 |
| 1.16 | SHW C | 1 | 4 | 2 |
| 1.17 | SHW C | 1 | 8 | 6 |
| 1.18 | SHW C | 1 | >50 | >50 |
| 1.19 | SHW C | 1 | >50 | >50 |

*Those compositions marked with an asterisk also showed foaming in the concentrate.

The concentrated compositions indicated in the above Table are given below. Where surfactants were supplied as aqueous solutions, the concentration of the surfactant solution as supplied is given first followed by the actual surfactant concentration in parentheses:

1.1 480 g/l glyphosate trimesium; 240 (156) g/l 2-ethyl-1-hexylglycoside (commercially available under the tradename BEROL AG6202-Akzo Nobel); 70 (35) g/l dioctyldimethylammonium chloride (commercially available under the tradename PENTONIUM DO 50 - Pentagon Chemicals).

1.2 As 1 but after storage for 2 months at 40° C.

1.3 As 1 but after storage for 2 months at −5° C.

1.4 (Comparison) 480 g/l glyphosate trimesium; 240 (156) g/l 2-ethyl-1-hexyl glycoside 1.5 (Comparison) A commercial concentrated composition containing 480 g/l glyphosate isopropylamine, available under the trade name ROUNDUP (Monsanto Corp).

1.6 (Comparison) A commercial concentrated composition containing 480 g/l glyphosate trimethylsulphonium and an anti-foam additive, available under the trade name TOUCHDOWN (Zeneca Limited).

1.7 (Comparison) A composition corresponding exactly to (6) above but without the anti-foam additive 1.8 (Comparison) 480 g/l glyphosate trimesium; 240 (156) g/l 2-ethyl-1-hexyl glycoside; 10 g/l polyethoxylated quaternary ammonium chloride (ETHOQUAD C25)

1.9 (Comparison) 480 g/l glyphosate trimesium; 240 (156) g/l 2-ethyl-1-hexyl glycoside; 8.6 (2.5) g/l N-alkyl trimethylammonium chloride (ARQUAD 16–29)

1.10 (Comparison) 480 g/l glyphosate trimesium; 240 g/l 2-ethyl-1-hexyl glycoside; 10 g/l ethoxylated tertiary amine (ETHOMEEN C12)

1.11 480 g/l Glyphosate trimesium; 240 (156) g/l 2-ethyl-1-hexylglycoside; 93.75 (75) g/l N-decyl,N-isononyldimethylammonium chloride (commercially available under the tradename BARDAC 2180 Lonza).

1.12 480 g/l glyphosate trimesium; 240 (156) g/l 2-ethyl-1-hexylglycoside (commercially available under the tradename BEROL AG6202 - Akzo Nobel); 70 (35) g/l dioctyldimethylammonium chloride (commercially available under the tradename QUERTON 28CL-50).

1.13 480 g/l Glyphosate trimesium; 240 (156) g/l 2-ethyl-1-hexylglycoside; 40 (20) g/l Di-isononyldimethylammonium chloride (commercially available under the tradename ALG 99- Millchem Ltd).

1.14 480 g/l Glyphosate trimesium; 240 (156) g/l 2-ethyl-1-hexylglycoside; 75 g/l n-hexyltrimethylammonium bromide 1.15 480 g/l Glyphosate trimesium; 240 (156) g/l 2-ethyl-1-hexylglycoside; 100 g/l n-octyltrimethylammonium bromide 1.16 480 g/l Glyphosate trimesium; 240 (156) g/l 2-ethyl-1-hexylglycoside; 100 g/l n-decyltrimethylammonium bromide 1.17 480 g/l Glyphosate trimesium; 240 (156) g/l 2-ethyl-1-hexylglycoside; 100 g/l n-dodecyltrimethylammonium bromide 1.18 (comparison) 480 g/l Glyphosate trimesium; 240 (156) g/l 2-ethyl-1-hexylglycoside; 75 g/l n-tetradecyltrimethylammonium bromide 1.19 (comparison) 480 g/l Glyphosate trimesium; 240 (156) g/l 2-ethyl-1-hexylglycoside; 285.71 (100) g/l N-cocotrimethylammonium chloride (commercially available under tradename ARQUAD C-35- Akzo Nobel)

Compositions 1.1 to 1.10 were subjected to a stability test involving storage at −5° C. and at 5° C. respectively for 1 month. Comparison compositions 1.4, 1.8, 1.9 and 1.10 all showed phase separation after this period. The remaining compositions of the invention showed no visible phase separation.

EXAMPLE 2

The following typical concentrated formulations of the invention showed no visible phase separation after storage for at least a month at ambient temperature, −5° C. and 40° C. respectively:

2.1 480 g/l glyphosate trimesium; 240 (156) g/l 2-ethyl-1-hexyl glycoside (commercially available under the tradename BEROL AG6202-Akzo Nobel); 70 (35) g/l dioctyldimethylammonium chloride (commercially available under the tradename QUERTON 28CL-50-Akzo Nobel).

2.2 480 g/l glyphosate trimesium; 180 (117) g/l 2-ethyl-1-hexyl glycoside (commercially available under the tradename BEROL AG6202-Akzo Nobel); 40 (20) g/l dioctyldimethylammonium chloride (commercially available under the tradename PENTONIUM DO 50-Pentagon Chemicals).

2.3 480 g/l glyphosate trimesium; 210 (136.5) g/l 2-ethyl-1-hexyl glycoside (commercially available under the tradename BEROL AG6202-Akzo Nobel); 63 (31.5) g/l dioctyldimethylammonium chloride (commercially available under the tradename PENTONIUM DO 50-Pentagon Chemicals).

2.4 480 g/l Glyphosate trimesium; 240 (156) g/l 2-ethyl-1-hexylglycoside (commercially available under the tradename BEROL AG6202-Akzo Nobel); 43.75 (35) g/l N-decyl, N-isononyldimethylammonium chloride (commercially available under the tradename BARDAC 2180 Lonza).

2.5 480 g/l glyphosate trimesium; 240 (156) g/l 2-ethyl-1-hexylglycoside (commercially available under the tradename BEROL AG6202-Akzo Nobel); 70 (35) g/l dioctyldimethylammonium chloride (commercially available under the tradename PENTONIUM DO 50-Pentagon Chemicals).

2.6 480 g/l Glyphosate trimesium; 240 (156) g/l 2-ethyl-1-hexylglycoside (commercially available under the tradename BEROL AG6202-Akzo Nobel); 40 (20) g/l Di-isononyldimethylammonium chloride (commercially available under the tradename ALG 99-Millchem Ltd)

2.7 480 g/l Glyphosate trimesium; 240 (156) g/l 2-ethyl-1-hexylglycoside (commercially available under the tradename BEROL AG6202-Akzo Nobel); 100 g/l n-octyltrimethylammonium bromide 2.8 480 g/l Glyphosate trimesium; 240 (156) g/l 2-ethyl-1-hexylglycoside (commercially available under the tradename BEROL AG6202-Akzo Nobel); 100 g/l n-decyltrimethylammonium bromide 2.9 480 g/l Glyphosate trimesium; 240 (156) g/l 2-ethyl-1-hexylglycoside (commercially available under the tradename BEROL AG6202 - Akzo Nobel); 100 g/l n-dodecyltrimethylammonium bromide

EXAMPLE 3

The foaming properties of a composition of the invention were evaluated under field conditions using typical farmer practice. A conventional tractor-mounted 1000 liter capacity spray tank was filled to 300 liters with water with the re-circulation pump running, the test concentrate (6 liters) was added and the tank was then filled to 600 liters to give a 1% w/w dilution. The re-circulation pump provided agitation for about a further minute before the tractor was driven on rough terrain for about 5 minutes. The test solution was totally sprayed out to leave residual foam, before the tank was partially re-filled with water to 200 liters to see if the residual foam dissipated. The compositions evaluated were Composition 2.1 of Example 2 and as comparison the commercial products ROUNDUP and TOUCHDOWN (the latter containing an anti-foam additive) as described under composition 1.5 and 1.6 of Example 1. The results were as follows:

|  | Foam Level | | |
| --- | --- | --- | --- |
| Evaluation Stage | Composition 2.1 | TOUCHDOWN | ROUNDUP |
| Completion of filling | Trace | Trace | 10 cm |
| After short journey | Trace | Trace | 6 cm |
| Spraying at 3001 | Trace | Trace | 12 cm |
| Spraying at 1001 | Trace | Trace | 15 cm |
| Spraying at 501 | Nil | Less than 1 cm | 15 cm |
| Tank empty | Nil | Trace | 18 cm |
| On refilling to 2001 | Nil | Nil | 6 to 7 cm |

TOUCHDOWN is a trademark of Zeneca Limited. ROUNDUP is a trademark of Monsanto Inc.

EXAMPLE 4

The activity of compositions of the present invention were compared with that of compositions containing no quaternary ammonium salt surfactant. Compositions were prepared from the following formulations:

4.1 An aqueous formulation containing 480 g/l glyphosate trimesium and 240 g/l alkylpolyglycoside surfactant available under the trade name AL2042.

4.2 An aqueous formulation containing 480 g/l glyphosate trimesium and 240 g/l BEROL AG6202 (See Comparison 1.4 above).

4.3 An aqueous formulation containing 480 g/l glyphosate trimesium, 239 g/l BEROL AG6202 and 70 g/l QUERTON 28CL-50 (see Example 1.12 above)

The herbicidal activity of the compounds was tested as follows: Required aliquots of each formulation were added to a 25 ml volumetric flask and made up to volume with tap water containing about 120 ppm calcium ion. This was sprayed in three replicates onto young pot plants giving a volume rate equivalent to 200 l/ha. Plants of each test species were then returned to warm or temperate glasshouse environments as appropriate for optimal growth.

Damage to plants was assessed at intervals after spraying by comparison with untreated plants, on a 0–100% scale where 0% is no damage and 100% is complete kill. Statistical analysis was carried out using simple linear regression (least squares method) to produce values of the rate required for 90% damage (referred to as $ED_{90}$). Relative potencies of each treatment were then calculated.

The test species used and the relevant abbreviations are as follows:

| | |
|---|---|
| AGRRE | Elymus repens |
| POANN | Poa annua |
| ELEIN | Eleusine indica |
| SORHA | Sorgum halepense |
| CHEAL | Chenopodium album |
| CONAR | Convolvulus arvensis |
| POLAV | Polygonum aviculare |
| EPHHL | Euphorbia heterophylla |
| CYPRO | Cyperus rotundus |

RELATIVE POTENCY ($ED_{90}$)

| | Grasses | | | |
|---|---|---|---|---|
| | AGRRE | POANN | ELEIN | SORHA |
| 4.1 | 1 | 1 | 1 | 1 |
| 4.2 | 1.00 | 0.43 | 0.67 | 0.66 |
| 4.3 | 0.99 | 0.93 | 0.83 | 0.72 |

| | Broad-leaved weeds | | | | |
|---|---|---|---|---|---|
| | CHEAL | CONAR | POLAV | EPHHL | ERICA |
| 4.1 | 1 | 1 | 1 | 1 | 1 |
| 4.2 | 0.65 | 1.35 | 1.24 | 0.89 | 1.65 |
| 4.3 | 0.73 | 0.95 | 1.47 | 0.95 | 1.04 |

| | Sedge CYPRO |
|---|---|
| 4.1 | 1 |
| 4.2 | 0.67 |
| 4.3 | 1.05 |

What is claimed is:

1. A low-foam, physically stable concentrated composition comprising (i) N-phosphonomethylglycine acid or a water-soluble salt thereof (ii) an alkylglycoside surfactant and (iii) a quaternary ammonium salt surfactant of formula $R^1R^2R^3R^4N^+X^-$ wherein $X^-$ is an agrochemically acceptable anion and either (i) $R^1$ and $R^2$ which may be the same or different are lower alkyl groups $R^3$ and $R^4$, which may be same or different, are branched or linear alkyl groups each containing from 6 to 18 carbon atoms or (ii) $R^1$ and $R^2$ and $R^3$ which may be the same or different are lower alkyl groups and $R^4$ is a branched or linear alkyl group containing 4 to 12 atoms.

2. A composition according to claim 1 wherein the alkylglycoside surfactant is 2-ethyl-1-hexyl glycoside having a degree of polymerisation of from 1 to 2.

3. A composition according to claim 1 wherein the quaternary ammonium salt surfactant is a dialkyldimethylammonium salt wherein $R^3$ and $R^4$ are alkyl groups wherein the sum of the carbon atoms in $R^3$ and $R^4$ is from 12 to 20.

4. A composition according to claim 3 wherein the quaternary ammonium salt surfactant is selected from dioctyldimethylammonium salts, N-decyl,N-isononyldimethylammonium salts and di-isononyldimethylammonium salts.

5. A composition according to claim 4 wherein the quaternary ammonium salt is dioctyldimethylammonium chloride and the alkylglycoside surfactant is 2-ethyl-1-hexyl glycoside having a degree of polymerisation of about 1.6.

6. A composition according to claim 1 wherein the quaternary ammonium salt is an alkyltrimethylammonium salt wherein $R^4$ is an alkyl group containing from 4 to 12 carbon atoms.

7. A composition according to claim 6 wherein the alkyltrimethylammonium salt is selected from n-octyltrimethylammonium salts, n-decyltrimethylammonium salts and n-dodecyltrimethylammonium salts.

8. A composition according to claim 1 wherein the concentration of the N-phosphonomethylglycine acid or a water-soluble salt thereof is from 50 to 500 g/l expressed as glyphosate acid equivalent.

9. A composition according to claim 1 wherein the concentration of the alkylglycoside is from 20 parts by weight of alkylglycoside per 100 parts by weight of glyphosate acid equivalent to 100 parts by weight of alkylglycoside per 100 parts by weight of glyphosate acid equivalent.

10. A composition according to claim 1 wherein the concentration of the quaternary ammonium salt surfactant is from about 1 part by weight of quaternary ammonium salt per 100 parts by weight of alkylglycoside to about 100 parts by weight of quaternary ammonium salt per 100 parts by weight of alkylglycoside.

11. A process of severely damaging or killing unwanted plants which comprises applying to the plants a herbicidally effective amount of a composition according claim 1.

* * * * *